US00PP24054P3

(12) United States Plant Patent
Barritt

(10) Patent No.: US PP24,054 P3
(45) Date of Patent: Dec. 3, 2013

(54) APPLE TREE NAMED 'WA 5'

(50) Latin Name: *Malus domestica*
Varietal Denomination: WA 5

(75) Inventor: Bruce H. Barritt, Okanagan Centre (CA)

(73) Assignee: Washington State University Research Foundation, Pullman, WA (US)

( * ) Notice: Subject to any disclaimer, the term of this patent is extended or adjusted under 35 U.S.C. 154(b) by 546 days.

(21) Appl. No.: 12/924,303

(22) Filed: Sep. 24, 2010

(65) Prior Publication Data

US 2012/0079638 P1 Mar. 29, 2012

(51) Int. Cl.
*A01H 5/00* (2006.01)

(52) U.S. Cl.
USPC ..... Plt./161

(58) Field of Classification Search
USPC ..... Plt./161, 172
See application file for complete search history.

(56) References Cited

PUBLICATIONS

Testing Agreement between Washington State University and Crane & Crane dated Apr. 27, 2007, 8 pages.
Testing Agreement between Washington State University and Wittenbach Orchards dated Apr. 24, 2007, 5 pages.

*Primary Examiner* — Kent L Bell
(74) *Attorney, Agent, or Firm* — Morrison & Foerster LLP

(57) ABSTRACT

A new and distinctive variety of a *Malus domestica* apple tree, named 'WA 5', that is distinguished by its attractive color of bright orange-red with distinct stripe over yellow background and exceptional eating quality, both fresh and after several months in common storage. WA 5 is homozygous for the ethylene production genes ASC1-2/2 and ACO1-1/1 which confer low ethylene production.

6 Drawing Sheets

Latin name of the genus and species of the claimed plant: Botanical/commercial classification: *Malus domestica*/apple tree.

Varietal denomination: 'WA 5'.

The invention refers to a new plant variety of apple tree (*Malus domestica*) named 'WA 5'. This new variety is distinguished by its distinctive apple color of bright orange-red with distinct stripe over yellow background. The new variety has exceptional eating quality, with good acid/sugar balance and outstanding crispness and juiciness that stays fresh even after several months in common storage due to the presence of the homozygous genes for ethylene production, ACS1-2/2 and ACO1-1/1.

BACKGROUND OF THE INVENTION

'WA 5' originated as a seedling from a cross between the maternal parent 'Splendour' and 'Coop 15' that was made at Corvallis, Oreg. in Year 1. The germinated seedling was grown in a greenhouse at Wenatchee, Wash. during the summer of Year 2. A bud from the original seedling was budded to 'M9' rootstock in the fall of Year 2 and maintained in a nursery row until the spring of Year 3, until the resulting tree was planted in the evaluation orchard at Wenatchee, Wash. Fruit from this originally budded tree was observed from Year 6, Year 7, and Year 8. Second generation 'WA 5' trees were chip-budded on 'M9' rootstock in Year 9 and planted at three central Washington locations in Year 11. Fruit from the 'WA 5' originally budded tree has been observed from Year 6 through Year 16, and fruit from second generation 'WA 5' trees has been observed from Year 12 through Year 16. No differences have been observed between fruit of the 'WA 5' originally budded tree and second generation trees, showing that 'WA 5' can be asexually propagated and remains true-to-type.

SUMMARY OF THE INVENTION

'WA 5' fruit is well suited for the fresh market as a commercial cultivar as both direct off the tree or out of medium to long term storage. The fruit of 'WA 5' is distinctly different from that of its parents in maturity timing, color and patterns, and shape. Differences in color and patterns, and shape between 'WA 5' and its parents 'Splendour' and 'Coop 15' are depicted in FIG. 6. Like its parent 'Splendour', 'WA 5' is homozygous for the ethylene production genes Md-ACS1 and Md-ACO1. The ACS and ACO genotypes were determined using the method described in Zhu and Barrit (2008). These genes confer low ethylene production, which contribute to the long shelf life and storage life of the apple. When compared to other major commercial varieties grown in Washington State, the overall flavor of 'WA 5' falls between the low acid varieties of 'Gala' and 'Fuji', and the high acid varieties of 'Braeburn' and 'Cripps Pink' (Table 1, fifth and sixth columns).

DETAILED BOTANICAL DESCRIPTION

Figure 1:
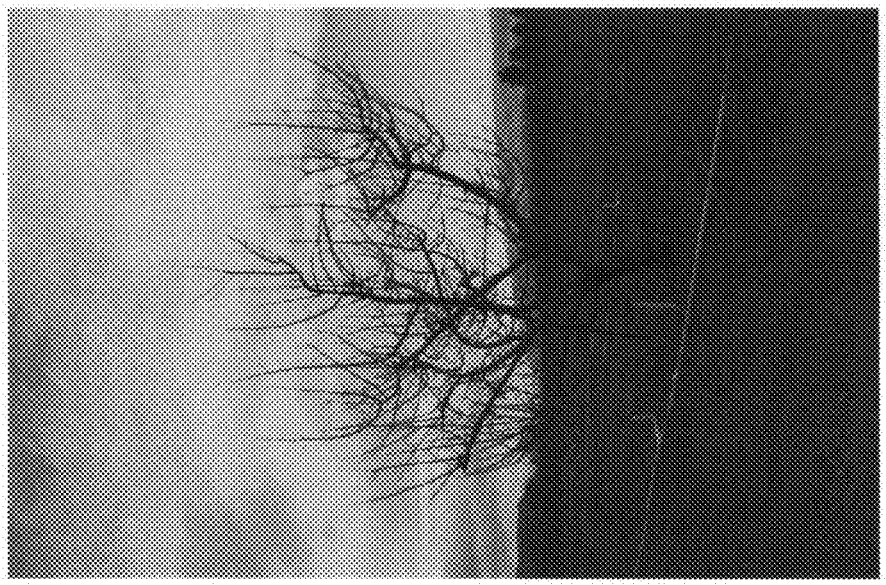
FIG. 1 depicts dormant 'WA 5' originally budded tree.
Figure 2:
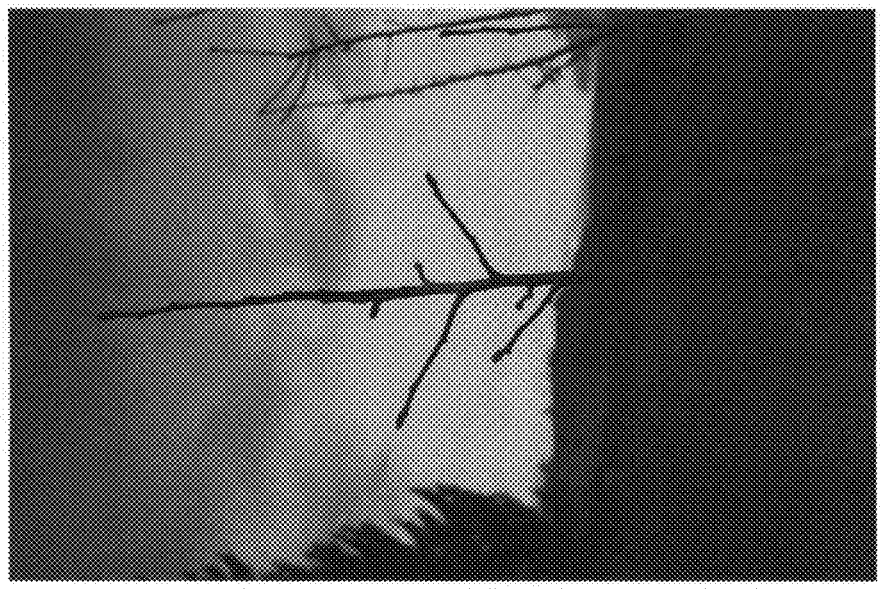
FIG. 2 depicts a fruiting branch of dormant 'WA 5' originally budded tree showing typical spur development and tip bearing nature.
Figure 3:
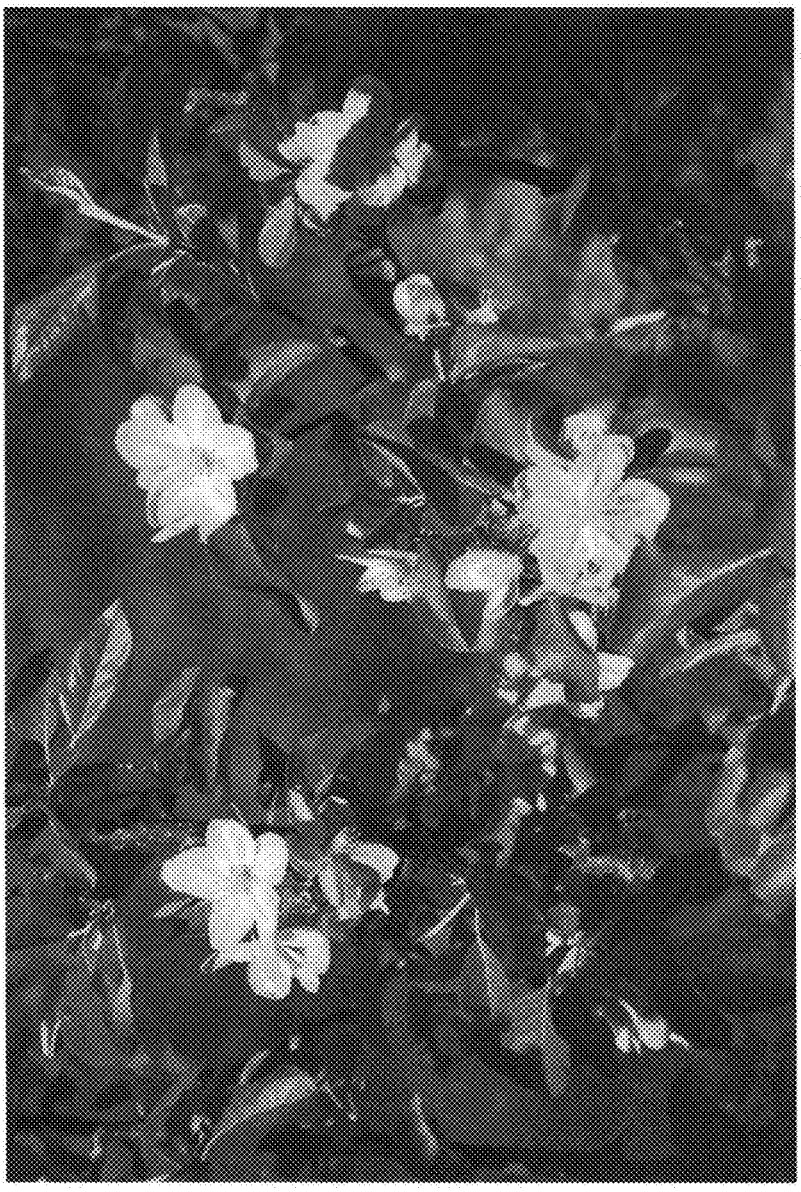
FIG. 3 depicts the 'WA 5' originally budded tree bloom at nearly full bloom stage.
Figure 4:
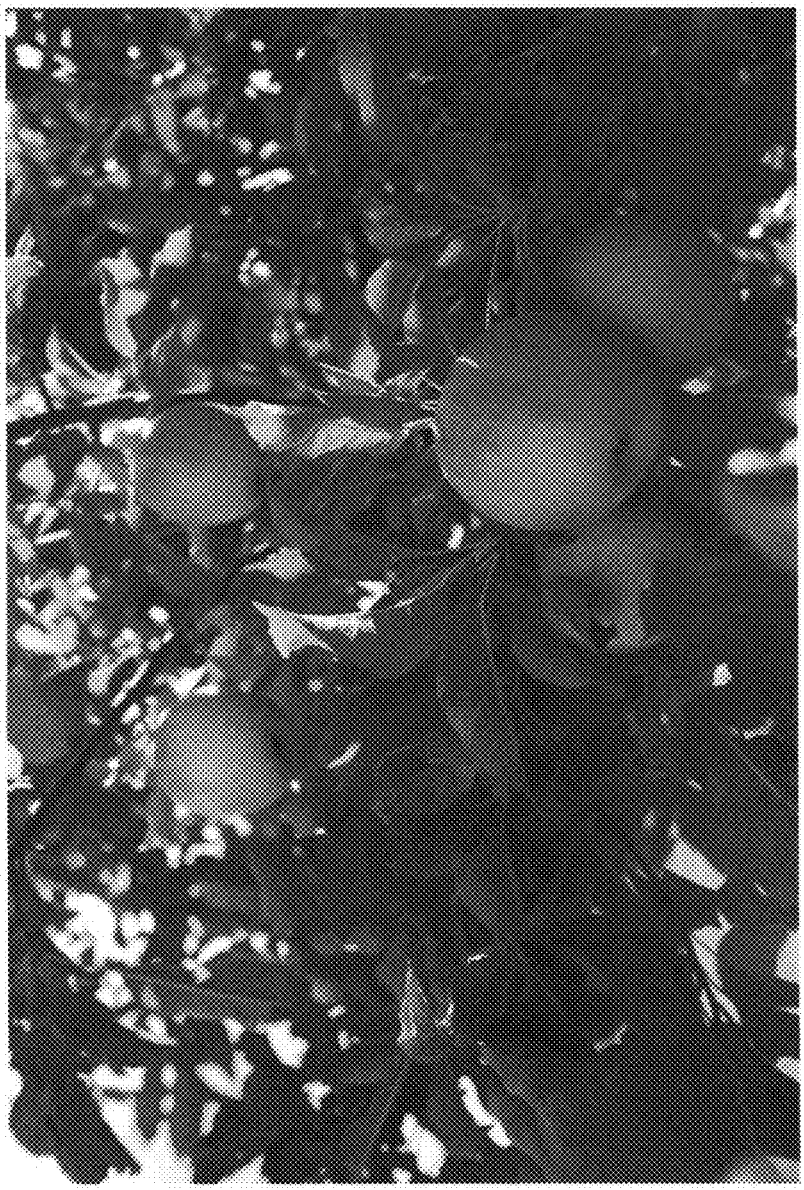
FIG. 4 depicts fruit from the 'WA 5' originally budded tree approaching harvest maturity.
Figure 5:
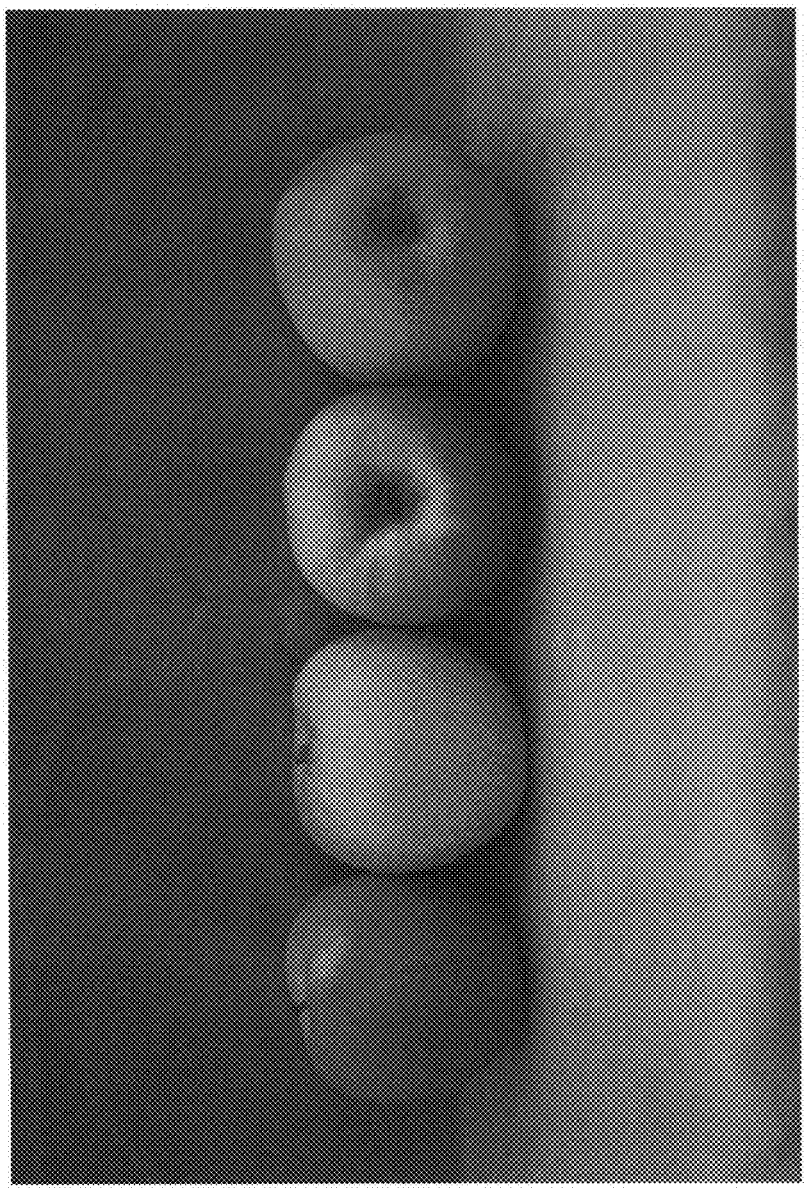
FIG. 5 depicts fruit from the 'WA 5' originally budded tree showing exposed side, back side, stem and calyx end views at harvest maturity.
Figure 6:
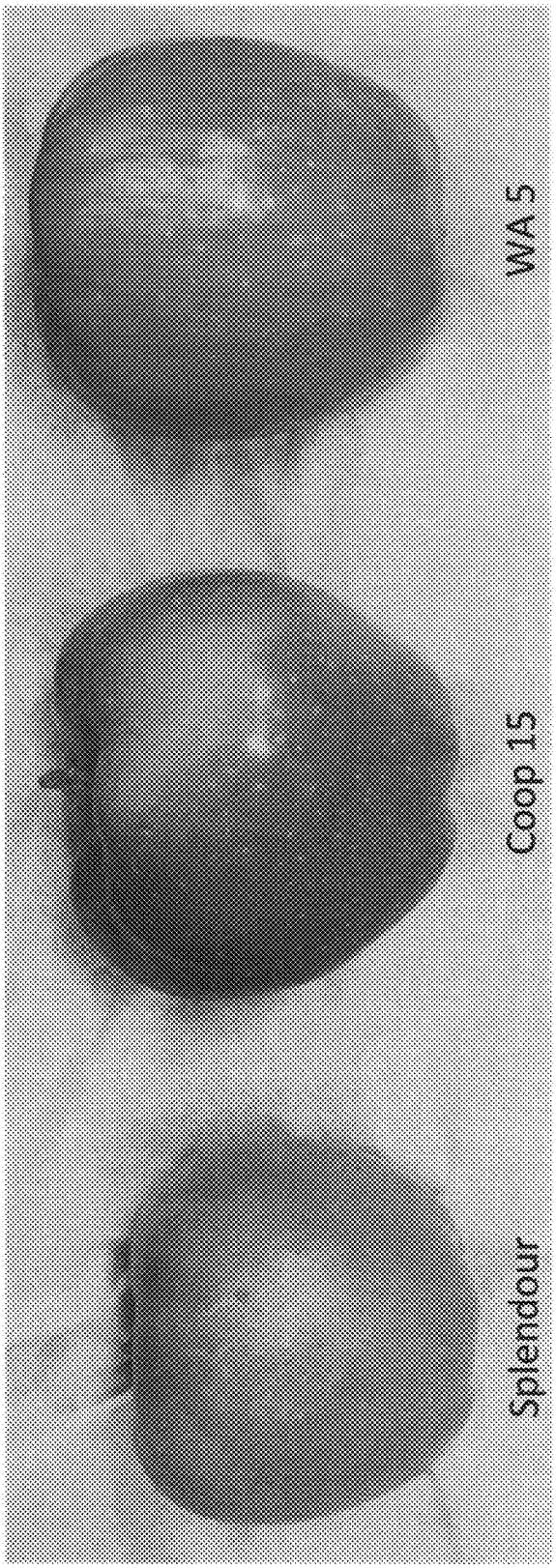
FIG. 6 depicts fruit of 'WA 5', 'Splendour', and 'Coop 15'. The fruit was harvested at the 'WA 5' harvest maturity date.

The following detailed description is from the 'WA 5' originally budded tree on 'M9' rootstock and grown at Wenatchee, Wash. for 12 years. All color references are from The R.H.S. Colour Chart by The Royal Horticultural Society.

Tree:

*Type*.—Training is an open vase type; it is a tip bearer with light to moderate spur development.

*Vigor*.—Considered moderate with seasonal growth averaging 38.5 cm.

*Overall shape*.—Upright and spreading.

*Height*.—12 feet.

*Width*.—8 feet.

*Hardiness*.—Considered hardy for the region, USDA hardiness zone is 7.

*Productivity*.—Very precocious and will have an alternate bearing tendency if cropped heavily the previous season.

Trunk:

*Size*.—Diameter at a height of 45 cm is 14 cm.

*Bark texture*.—Rough.

*Bark color*.—From the black group 202A.

*Lenticelsl*.—Present and moderate in number, averaging 6 per 16 $cm^2$; average width is 9.6 mm; and average height is 2.1 mm.

*Lenticels color*.—From the greyed-purple group N186A.

Branches:

*First year branches*.—Diameter: At mid-point of growth averages 5.1 mm. Color: From the greyed-orange group 76A. Lenticels: Are numerous averaging 25 per running cm of growth; are round and range from 0.8 mm to 1.0 mm in diameter; and color is from the white group 155A. Branch pubescence: Is present on the terminal ⅔rds of the growth; and color is from white group 155D. Internodes: Length ranges from 2.6 cm to 3.9 cm with an average of 3.2 cm.

*Two year old fruiting branches*.—Diameter: At mid-point of growth averages 8.4 mm. Spur development: Considered moderate on the light side; spurs are elongated and range in length from 0.5 cm to 10 cm in length. Lenticels: Numerous, averaging 14 per running cm and are round to slightly elongated being 1 mm in diameter or 2 mm in width by 1 mm in height.

*Scaffold branches*.—Size: Ranges from 7 cm to 10 cm in diameter as measured 10 cm from trunk. Angle: Moderate to flat — ranging from 60 to 90 degrees from vertical. Color: Color is from the greyed-green group 197A. Lenticels: Moderate in number, averaging 1 per square cm. Shape and size: Elongated and averaging 8.1 mm in width and 2.3 mm in height. Lenticels color: Color is from the greyed-orange group 166D.

Leaves:

*Shape*.—Oval.

*Texture*.—Smooth, leather upper surface.

*Sheen*.—Glossy upper surface.

*Pubescence*.—Lower surface has light white pubescence present.

*Length*.—Blade length ranges from 9.7 cm to 11.5 cm with an average of 10.6 cm.

*Width*.—Ranging from 5.7 cm to 6.8 cm with an average of 6.1 cm.

*Margin*.—Double Serrate.

*Tip*.—Cuspidate.

*Base*.—Rounded.

*Stipules*.—Small and not present on all leaves; ranges from 3.25 mm to 8.3 mm long and from 0.7 mm to 1.2 mm wide; color on upper surface is from the green group 137A; and color on lower surface is from the green group 138B.

*Leaf color*.—Upper surface is from the green group 137A; lower surface is from the green group 138B.

*Mid-vein*.—Prominent with considerable white downiness on under surface; width at mid blade averages 1.4 mm; upper surface color is from the green-white group 157C; and lower surface color is from the green-white group 157D.

*Petiole*.—Length: Ranges from 32.2 mm to 41.1 mm with an average of 36.3 mm. Diameter: Ranges from 1.6 mm to 1.8 mm with an average of 1.7 mm. Color: From the green group 138D, with highlights from the greyed-purple group 185B at the basal end. Pubescence: Abundant over the entire length and circumference and the color is from the greyed-yellow group 161A.

*Flower buds*.—Shape is conic; base is considered truncate and the tip is rounded; length ranges from 0.6 cm to 0.9 cm with an average of 0.85 cm; diameter at base ranges from 0.3 cm to 0.55 cm with an average of 0.45 cm; and color is from the greyed-orange group 176A.

Flowers: Full bloom date was May 5 of Year 16, with 5 year average being April 29, at Wenatchee, Wash.; number of blossoms per cluster ranges from four to five; total depth with petals folded ranges from 16.1 mm to 20.2 mm with an average of 19.5 mm, or 2 mm to 4 mm with an average of 3 mm from base of ovary to petal base.; and aroma is typical of apple blossom, mildly sweet aromatic.

*Size*.—Considered medium, when fully expanded, diameter ranged from 45.9 mm to 53.8 mm, with an average of 49.7 mm.

*Petal*.—Width averages 17.1 mm; length averages 22.0 mm; petal number is 5; shape is obovate with rounded tip and base, and margin is smooth as are both upper and lower surfaces.

*Color*.—Both upper and lower petal surfaces are from the white group 155D, with highlights on the lower surface from the greyed-purple group 186C; petal vein color from the greyed-purple group 186B for both the upper and lower surfaces.

*Stamen*.—Number ranges from 17 to 20 with an average of 19.

*Filament*.—Length ranges from 8.1 mm to 12.6 mm; and color is from the white group 155C.

*Anthers*.—Heart shaped that is 1.5 mm wide×1.7 mm long; and mature color is from the greyed-yellow group 160A.

*Pistil*.—One imperfectly syncarpic pistil per flower, length ranges from 11.6 mm to 13.2 mm with an average of 12.1 mm.

*Styles*.—Five in number, fused at base and pubescent at union; average length is 3.1 mm; and color is from the greyed-yellow group 160C.

*Stigma*.—Club shaped. Color is from the greyed-yellow group 160A. Typical and observed stigma had an average width of 0.73 mm.

*Sepals*.—Five per blossom and occasionally curled back towards the peduncle; shape is considered deltoid with the tip being acuminate and the base being truncate; average length is 7.9 mm; average width is 3.9 mm; abundant colorless pubescence is present on both upper and lower surface; sepal color is from the green group 143C with tips highlighted from the greyed-red group 174A for both the upper and lower surfaces; and typical and observed sepal margin is smooth.

*Peduncle*.—Length ranges from 16.3 mm to 20.2 mm with an average of 18.6 mm; color is from the green group 138A; and considerable downy hair is present over the entire surface.

*Pollen*.—Considered moderate in amount with color from the yellow group 160B.

Fruit: Observations and testing from originally budded tree fruit; fruit is considered precocious; and in the fifth year after planting, fruit yield was 32.8 kg (186 fruits).

*Form*.—Considered round-conical; equatorial diameter cross section is irregular, exhibiting an angular outline.

*Size*.—Considered medium with a normal crop level; averaging 7.7 cm in equatorial diameter and 7.2 cm in axis diameter. Average single fruit weight: 176.3 g.

*Stem*.—Considered medium short — barely reaching above the stem bowl with an occasional stem not reaching above the stem bowl; stem is considered medium stout with an average length of 17 mm and an average diameter of 2.7 mm; and color is from the greyed-green group 197A.

*Stem cavity*.—Average width is 3.2 cm and average depth is 1.4 cm.

*Cavity shape*.—Acute.

*Lipped*.—No.

*Basin cavity*.—Average width is 24.2 mm and average depth is 7.1 mm and puckered around eye and texture is downy at the base. Ribbed: yes. Eye: Erect convergent with tendency towards connivent; and sepals are downy in texture.

*Skin*.—Smooth with bloom present.

*Appearance*.—Bicolor with distinct mottled stripe.

*Skin color*.—Overcolor from the red group 45A; overcolor from the red group 46A; and undercolor from the yellow group 8C.

*Lenticels*.—Present and distinct with an average of 4 per $cm^2$; are smooth with the skin; and color is from the white group 155D.

*Lenticels size*.—Round and ranging from 0.3 mm to 0.6 mm in diameter.

*Core*.—Standard 5 locules, each 4 mm wide, 1.5 cm long, with elongated teardrop shape; total core width 3 cm, length 7 cm. Core position: Considered distant. Core Line position: Median.

*Cell*.—Tufted: Very little to none. Cell Shape: Ovate.

*Tube*.—Cone shaped.

*Stamen position*.—Median.

*Axis*.—Is axial and closed.

*Seed*.—Number: Number per locule: mostly three with an occasional 2. Average number per fruit: 15. Shape: Acuminate. Average length is 8.9 mm and average width is 4.2 mm. Color: From the greyed-orange group 166A.

*Flesh*.—Is firm, crisp and juicy; and color is from the yellow group 2D.

*Aroma*.—Mild, apple like.

*Date of harvest maturity*.—September 14 of Year 16.

*Maturity indices*.—Starch: 4. Pressure: 91.2 Newtons. Soluble Solids: 15.2° Brix. Titratable Acid: 0.57 mg/l of malic acid.

*Genotype*.—For the Md-ASCI ethylene production gene, 'WA 5' is homozygous ASC1-2/2; for the less significant ethylene production gene Md-ACO1, 'WA 5' is homozygous 1/1.

*Keeping quality*.—Excellent, greater than 60 days in common storage.

*Eating quality*.—Exceptional with good acid/sugar balance and outstanding crispness and juiciness.

Pollination: Any diploid apple of the same bloom period.

Use: Primarily a fresh market dessert apple.

Disease and insect resistance: 'WA 5' is susceptible to apple powdery mildew and fire blight.

Table 1 represents differences in harvest parameters of the 'WA 5', 'Gala', 'Fuji', 'Braeburn', and 'Cripps Pink' varieties at harvest maturity and following 60 days in common storage. The parameters include firmness measured in Newtons, sugar measured as ° Brix, and acidity measured as mg/l of malic acid.

TABLE 1

Differences of harvest parameters at harvest and 60 days in common storage

| Cultivar | Firmness (Newtons) | Firmness 60 (Newtons) | Sugar (° Brix) | Acidity (mg/l of malic acid) | Acidity 60 (mg/l of malic acid) |
|---|---|---|---|---|---|
| WA 5 | 91.2 | 78.7 | 15.2 | 0.57 | 0.52 |
| Gala | 67.7 | 67.8 | 14.1 | 0.45 | 0.43 |
| Fuji | 75.3 | 68.6 | 14.5 | 0.49 | 0.44 |
| Braeburn | 95.4 | 88.8 | 12.6 | 0.74 | 0.67 |
| Cripps Pink | 94.7 | 87.7 | 14.9 | 1.18 | 0.9 |

What is claimed:

1. A new and distinct variety of apple tree named 'WA 5', as herein shown and described.

* * * * *